United States Patent
Bod et al.

(10) Patent No.: US 6,770,786 B1
(45) Date of Patent: Aug. 3, 2004

(54) PROCESS FOR PREPARING A SUBSTITUTED ALLYLAMINE DERIVATIVE AND THE SALTS THEREOF

(75) Inventors: Peter Bod, Gyömrő (HU); Laszlo Terdy, Budapest (HU); Ferenc Trischler, deceased, late of Budapest (HU), by Ferenc Trischler, Jr., Tamás Trischler, heirs; Eva Fekecs, Budapest (HU); Maria Demeter, Budapest (HU); Anna Lauko, Budapest (HU); Gyorgy Domany, Óbánya (HU); Gyorgyi Szabone Komlosi, Budapest (HU); Katalin Varga, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 0 days.

(21) Appl. No.: 10/110,724
(22) PCT Filed: Oct. 22, 1999
(86) PCT No.: PCT/HU99/00071
§ 371 (c)(1), (2), (4) Date: Feb. 21, 2003
(87) PCT Pub. No.: WO01/28976
PCT Pub. Date: Apr. 26, 2001
(51) Int. Cl.⁷ ............................................. C07C 209/08
(52) U.S. Cl. ...................................... 564/386; 564/337
(58) Field of Search .................................. 564/337, 386

(56) References Cited

U.S. PATENT DOCUMENTS 5,021,446 A   6/1991   Meki et al. .................. 514/407

FOREIGN PATENT DOCUMENTS

EP   0 341 048        11/1989
HU   209 284    *    4/1994    .......... C07C/211/25

OTHER PUBLICATIONS

Database CAPLUS on STN, Acc. No. 1996:155213, Dalla Croce et al., Gazzetta Chimica Italiana (1996), 126(2), p. 107–9 (abstract).*
Database CASREACT on STN, No. 124:342737, Dalla Croce et al., Gazetta Chimica Italiana (1996), 126(2), p. 107–9 (abstract).*

Nussbaumer et al. "*Allylamine Antimycotics: Recent Trends in Structure—Activity Relationships and Syntheses*", Pestic. Sci. 31, 437–455 (1991).

* cited by examiner

Primary Examiner—Brian J. Davis
(74) Attorney, Agent, or Firm—Keil & Weinkauf

(57) ABSTRACT

The antifungal agent (E)-N-methyl-N-(1-naphthylmethyl)-6,6-dimethyl-hept-2-ene-4-ynyl-1-amine of formula (I)

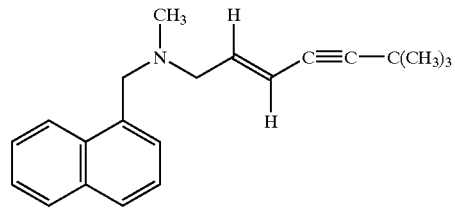

(I)

and acid addition salts thereof are prepared by reacting a chloro-compound of formula (IIIb)

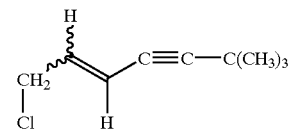

(IIIb)

with a secondary amine of formula (II)

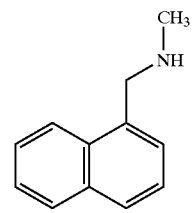

(II)

in an aliphatic ketone-type solvent in the presence of a base and optionally iodide salt catalyst, and subsequently treating the resulting reaction mixture directly with aqueous hydrochloric acid to precipitate the hydrochloride of the compound of formula (I). The precipitate is separated, and the base of formula (I) can be liberated from the hydrochloride and can be converted into other pharmaceutically acceptable acid addition salts.

10 Claims, No Drawings

PROCESS FOR PREPARING A SUBSTITUTED ALLYLAMINE DERIVATIVE AND THE SALTS THEREOF

The invention relates to a new process for preparing the (E)-N-methyl-N-(1-naphthylmethyl)-6,6-dimethylhept-2-ene-4-ynyl-1-amine of formula (I) and the acid addition salts thereof.

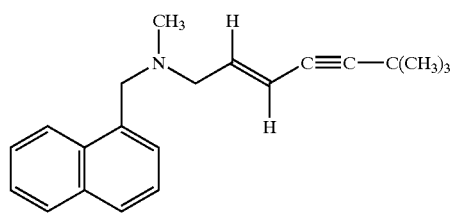
(I)

The compound of formula (I)—international nonproprietary (INN) name: terbinafine—was first disclosed in the European Patent Specification No. 24587 (priority: 22.08.1979) as a good antifungal agent used preferably against mycosis caused by dermathophytons on the skin and on the nail. Example 16 of this patent specification describes the specific compound and mentions that it is a trans isomer. According to the patent specification the terbinafine was prepared in three different chemical ways. It can be seen from the specification that the compound was always obtained in base form—namely as the mixture of cis(Z) and trans(E) isomers. The separation was achieved by column chromatography which is a procedure preferably not employed in an industrial large scale production.

In a later publication (see J. Med. Chem. 27, 1539–1543 (1984)) the hydrochloride salt of the trans isomer was obtained from the mixture of the base by way of column chromatography on silica-gel, and salt formation with hydrochloric acid in ethanol followed by re-crystallization. After the success of terbinafine on the market more processes were published. Thus the process described in Swiss Patent Specification No. 678 537 or in its Hungarian equivalent Pat. No. 209 284 used as starting material the hydrochloride salt of N-methyl-1-naphthalenemethylamine of formula (II) and the geometric isomeric (E:Z) mixture of 3:1 of 1-bromo-6,6-dimethyl-hept-2-ene-4-yne of formula (IIIa).

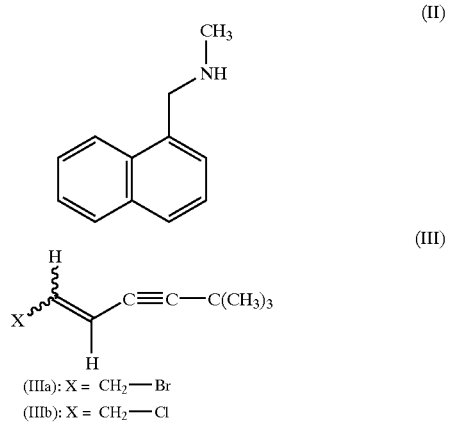
(II)

(III)

(IIIa): X = CH₂—Br
(IIIb): X = CH₂—Cl

The essence of the procedure is that the secondary amine was alkylated with the bromo-compound of formula (IIIa),—a crude product and mixture of geometric isomers—in the presence of aqueous sodium-hydroxide. The terbinafine base was formed as the mixture of trans- and cis-isomers in form of an oily substance. The crude terbinafine (still a mixture of isomers) was obtained by extraction with toluene and by evaporation of toluene, and had the same ratio of isomers as the compound of formula (IIIa). The crude terbinafine was then dissolved in ethyl acetate and hydrochloric acid gas was introduced into the solution. After stirring for a long time (4–15 hours) the precipitated hydrochloride salt of trans-terbinafine product of formula (I) was centrifuged, washed with ethyl acetate and dried.

The disadvantages of the process are the necessity to work with the offensive and unstable bromo-compound of formula (IIIa) and with the poisonous, aromatic solvent (extraction and evaporation of toluene), and that the preparation of the hydrochloride salt of terbinafine product requires dry hydrochloric acid gas and anhydrous ethyl acetate as solvent.

The compound of formula (IIIb) is an analogue of the known bromo-compound of formula (IIIa) (see European Patent Specification No. 341 048). It was prepared from known 3-hydroxy-6,6-dimethyl-hept-1-ene-4-yne of formula (IV), but no characteristic data of the chloro-compound of formula (IIIb) were described. (IIIb) was reacted directly, in form of a residue obtained by evaporation, with N-hydroxy-phthalimide. It is important to note that the chloro-compound of formula (IIIb) was not described elsewhere in the literature.

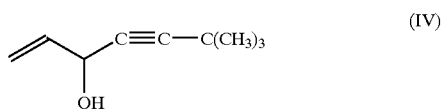
(IV)

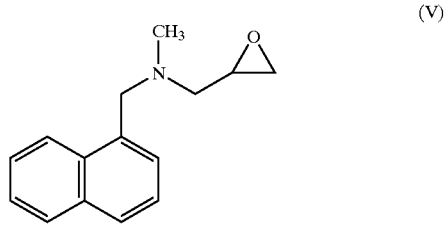
(V)

A different synthetic principle was applied in the preparation of terbinafine described in the Canadian Patent Specification No. 2 185 599. Here the epoxide of formula (V) was obtained from the secondary amine of formula (II) with an excess of epichlorohydrin, and (V) was converted into the secondary alcohol of formula (VI). Dehydration of the secondary alcohol of formula (VI) yielded a mostly undefined geometric isomeric mixture of (I).

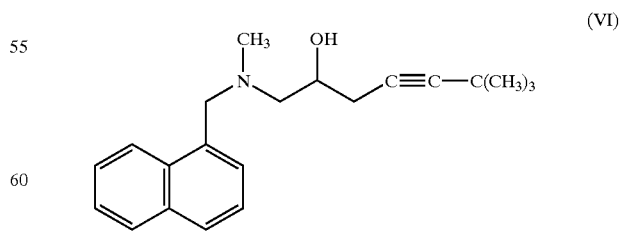
(VI)

According to another process, the aldehyde derivative of formula (VII), obtained from the secondary amine of formula (II), was reacted with the phosphorus-compounds of formula (VIII) in a Wittig-type reaction. This process also resulted in an undefined isomeric mixture of the compound (I).

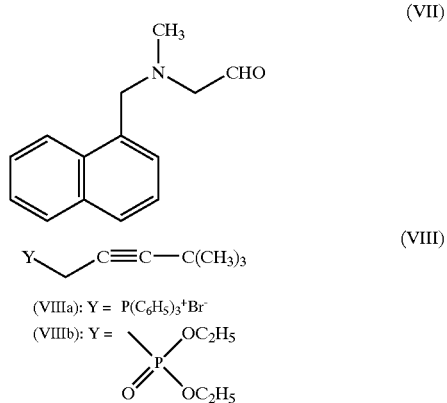

The two processes above have several disadvantages:
- a large excess of reagents (epichlorohydrin, 3,3-dimethyl-butyne) were required;
- occasionally, undefined amounts and ratios of reagents were used;
- complicated isolations by column chromatography were necessary;
- the product was obtained in form of a very disadvantageous (and eventually undefined) geometric isomeric mixture (E:Z 1:9→11).

The object of this invention is a process which does not have the disadvantages of the known processes and which is applicable for large scale production.

During our experiments it was surprisingly found that the acid addition salt of terbinafine may be prepared, without isolating the base form of compound of formula (I), by reacting the known secondary amine of formula (II) and the secondary alcohol of formula (IV) in a specific solvent.

This observation led to further unexpected results:

a) Reaction of the secondary alcohol of formula (IV) and cc. hydrochloric acid yields the chloro-derivative of formula (IIIb) quantitatively, whereas, in accordance with the procedure disclosed in the European Patent Specification No. 341 048 which employs thionyl chloride, this compound could only be obtained in a crude yield of 88%.

b) The quantitative formation of the compound of formula (IIIb) is surprising because the aqueous hydrogen chloride which is used for the preparation of (IIIb) is less reactive than the hydrobromic acid which is used for the preparation of the compound of formula (IIIa).

c) In the reaction with HCl instead of HBr, the less space requiring Cl-atom attaches to the end of the molecule. The trans:cis isomeric ratio obtained is not getting worse at all, it is even a little better (3:1→3.4:1).

d) It is also surprising that the reactivity of the chloro-compound of formula (IIIb) is similar, or even a little better than, the reactivity of the known bromo-analogue. Namely, the alkylation of the amine of formula (II) generated the product of formula (I) in a good yield.

e) The use of aliphatic ketones as a type of solvent gave an unexpected and surprising result. This solvent type is excellent for the extraction of the alkylating agent of formula (IIIb) and proved to be an effective solvent for the preparation of the compound of formula (I).

Furthermore, when an aliphatic ketone, especially methyl isobutyl ketone, is used as a solvent, the hydrochloride salt of the end-product surprisingly precipitates after acidification with hydrogen chloride while the undesired hydrochloride salt of the cis-isomer and the other chemical impurities of the end-product remain in the solution and can be removed easily.

Table 1 summarizes the cis-isomer content of end-products obtained in different solvents. The results demonstrate that our surprising recognition, namely the advantageous use of an aliphatic ketone, especially methyl isobutyl ketone, afforded an especially low percentage of cis-isomer impurity.

Terbinafine base as a mixture of isomers of 75 w % trans and 25 w % cis was used as starting material.

TABLE 1

| Used solvent | Cis-isomer % of the obtained terbinafine salt |
| --- | --- |
| toluene | 10.7 |
| n-hexane | 11.7 |
| di-isopropyl-ether | 18.9 |
| ethanol | 10.6 |
| methyl isobutyl ketone | 0.19 |

Therefore, on the basis of the above goals, the invention is a new process for the preparation of the amine of formula (I) and acid addition salts thereof. This may be carried out as follows: the chloro-compound of formula (IIIb)—containing the E and Z isomers in a weight-ratio of 3.3–3.4:1—is prepared by reacting the secondary alcohol of formula (IV) with hydrogen chloride in a solvent. Then (IIIb) is reacted with the secondary amine of formula (II) in an aliphatic ketone-type solvent in the presence of a base and optionally a iodide salt catalyst. The compound of formula (I) is obtained in base form and in an isomeric ratio of 3.3–3.4:1. The base is converted directly into the hydrochloride salt by adding aqueous hydrogen chloride. The E-isomer-hydrochloride precipitates and is separated. Optionally the base can be liberated and can be converted—in a known way—into an acid addition salt with another pharmaceutically acceptable acid.

In a preferable embodiment of the process according to the invention 3–7 mole of the secondary alcohol of formula (IV) are reacted with preferably 5.0–5.5 mole, preferably ice cooled, cc. hydrochloric acid. Conveniently, the reaction mixture is stirred overnight.

The chloro-compound of formula (IIIb) is obtained as a geometric isomeric mixture—the weight-ratio of trans:cis (E:Z) is 3.3–3.4:1-, and is extracted with an aliphatic ketone-type solvent, preferably methyl isobutyl ketone. Then the chloro-compound of formula (IIIb) extract is diluted with methyl isobutyl ketone and is reacted with the amine of formula (II). This alkylation reaction is carried out in the presence of an amine-base at 20–80° C. for 1–16 hours, preferably in the presence of equimolar N,N-diisopropylethylamine and 5–7 mole % iodide-salt catalyst for 3–5 hours.

The base form of the compound of formula (I) is obtained in solution in the phase of methyl isobutyl ketone, and is converted into a hydrogen-chloride salt by adding aqueous hydrochloric acid. The pH of the mixed two-phase system is adjusted to 1.0–3.0, preferably to 1.5–2.0. Then the two-phase system is cooled with stirring. The precipitated solid is filtered off, washed with water and with methyl isobutyl ketone and dried. The obtained hydrochloride salt—containing the desired E isomer—is treated with a base, e.g. ammonium-hydroxide, under mild conditions.

The base of formula (I) obtained this way is converted into an acid addition salt by treatment with a pharmaceutically acceptable acid.

One of the starting materials of the process according to our invention, the secondary alcohol of formula (IV), is a known compound. This compound may be prepared e.g. according to the EP 24 587 Patent Specification using 3,3-dimethyl-1-butyne and acrolein. (See J. Med. Chem. 27, 1539–42 (1984))

The other starting material of the process according to our invention—the secondary amine of formula (II)—was described as a hydrochloride salt in Beilstein 12, II. 740, III. 3097, and IV. 2192.

Summarized, the process according to our invention has the following advantages:

1) The secondary alcohol of formula (IV) is converted into the alkylating chloro-compound of formula (IIIb) in a simple way by using cc. aqueous hydrogen chloride.

2) The compound of formula (IIIb) is obtained quantitatively from the reaction mixture by a single extraction with aliphatic ketone and can be reacted further in the same medium. The hydrochloride of the end-product of formula (I) simply precipitates from the aqueous-ketone, two-phase reaction mixture in the final acidification with hydrochloric acid.

3) The ketone, preferably methyl isobutyl ketone, used by us in the reaction steps has three functions in the process: it is an extracting agent, a solvent and finally a cosolvent, keeping the apolar, hardly water soluble impurities of the end-product in solution.

4) Compared to the processes of the prior art, our process is simple and suitable for large scale operations. The secondary alcohol of formula (IV) may be added to the apparatus and the hydrochloride of the compound of formula (I)—as the pure (E) trans isomer—is obtained at the end of the process.

5) While the processes of the prior art use hydrochloric acid gas for converting compound of formula (I), our process uses the more suitable aqueous hydrochloric acid.

6) In our process the hydrochloride salt of the end-product precipitates from a heterogeneous, two-phase (upper ketone, lower acid-aqueous) system. This provides for the high purity of the product obtained by the process according to the invention. The total impurity of the product (see Example 1, where it is 0.19%) is less, than the level of impurity obtained in the processes of the prior art (0.3%). Moreover the end-product does not contain—because it can not—bromide impurity.

7) Our process does not require expensive, anhydrous solvents.

EXAMPLE 1

Step A

Preparation of 1-chloro-6,6-dimethyl-hept-2-ene-4-yne 54 g (0.54 mole, 46 ml) cc. hydrochloric acid were added drop-wise to 13.82 g (0.1 mole) 6,6-dimethyl-hept-1-ene-4-yn-3-ol of formula (IV) with stirring and ice cooling at 2–6° C. After 8 hours stirring under ice-cooling the reaction mixture was further stirred overnight (15–16 hours).

40 g (50 ml) methyl isobutyl ketone were added to the two phase system. After, separating the lower acid-water phase, the upper organic phase was extracted three times with 10 g water. After separating the aqueous phase the 1-chloro-6,6-dimethyl-hept-2-ene-4-yne of formula (IIIb) was obtained practically quantitatively—in the form of a mixture of trans-cis isomers—as an acid free methyl isobutyl ketone extract.

Step B (E)-N-methyl-N-(1-naphthylmethyl)-6,6-dimethylhept-2-ene-4-ynyl-1-amine-hydrochloride 17.4 g (0.1 mole) N-methyl-1-naphthalenemethylamine of formula (II), 13.0 g (0.1 mole) N,N-diisopropylethylamine, 26 g ion free water and 22.22 g (0.006 mole) tetrabutylammonium-iodide were added in the given order to the methyl isobutyl ketone extract obtained in step A, and the mixture was stirred from 4 hours at 70–80° C. The mixture was cooled to room temperature. After diluting with methyl isobutyl ketone the lower aqueous phase was separated. 15.5 g (13 ml) cc. hydrochloric acid were added drop-wise to the upper organic phase with stirring at 16–20° C.

After crystallization started, the reaction mixture was stirred for 1–2 hours at room temperature, then further for 1–2 hours at 2–6° C. The product was filtered off, washed twice with water, and once with methyl isobutyl ketone. After drying, 17.5 g (53.37%) terbinafine-hydrochloride salt were obtained (based on the secondary alcohol of formula (IV) used in Step A).

Melting point: 205–207° C.

Total impurity (by HPLC method): 0.19%

EXAMPLE 2

The reaction was conducted in the same manner as Example 1 with the difference that the reaction described in Step B was carried out without tetrabutylammonium iodide.

Yield: 16.1 g (49.1%).

Melting pint: 205–207° C.

Total impurity (by HPLC method): 0.195%.

EXAMPLE 3

The reaction was conducted in the same manner as Example 1 with the difference that 17.5 g terbinafine-hydrochloride obtained in Step B were converted into the base by adding aqueous ammonia. The obtained product was reacted with 5 g lactic acid. 18.5 g terbinafine-lactate were obtained.

EXAMPLE 4

14.3 g 6,6-dimethyl-1-heptene-4-yn-3-ol (96%, equivalent to 0.1 mole 100%) were placed in a 250 ml flask. Then 54 g (46 ml, 0.54 mole) cc. hydrochloric acid were added drop-wise with stirring under nitrogen atmosphere at 0–(−2)° C. The reaction mixture was stirred for 22 hours at this temperature. Then the reaction mixture was allowed to warm to 20–25° C. and 40 ml methyl isobutyl ketone were added and stirred for 15 minutes at this temperature. The organic layer was separated, then washed with 4×20 ml water. Then 20 ml methyl isobutyl ketone, 17.4 g (0.1 mole) N-methyl-1-naphthylmethyl-amine, 12.9 g (17.5 ml, 0.1 mole) N,N-diisopropylethylamine, 26 ml water and 2.2 g tetrabutylammonium iodide were added under nitrogen during a period of 1 hour and stirred without cooling and heating. The mixture was heated to 70–80° C. and stirred for 1 hour. The reaction mixture was cooled to 20–25° C. and 40 ml methyl isobutyl ketone were added. The organic layer was separated and 10 ml hydrochloric acid were added with stirring at 15–20° C. The mixture was stirred for 2 hours at this temperature after crystallization started. Then it was cooled to 5–10° C. and stirred for 1 hour.

The obtained crystals were filtered off, washed with 2×20 ml 5° C. water, then 2×20 ml 5° C. methyl isobutyl ketone. The wet product was suspended in the mixture of 100 ml methyl isobutyl ketone and 7 ml of water. 6.9 ml 25% ammonium-hydroxide were added drop-wise at 20–25° C. and stirred for 15 minutes. The solution was filtered though a glass filter and the layers were separated. 9.2 ml 6 N hydrochloric acid was added drop-wise to the solution and stirred for 1 hour at this temperature, then further for 1 hour at 5–10° C. The product was filtered off, washed with 2×20 ml 5° C. water and 2×20 ml 5° C. methyl isobutyl ketone. The product was air-dried at 40° C.

Yield: 16.9 g (51.5%).

Melting point 204–205° C.

Impurity (cis-isomer): less than 0.1%.

EXAMPLE 5

14.3 g 6,6-dimethyl-1-heptene-4-yn-3-ol were placed in a 250 ml flask, and then 54 g (46 ml, 0.54 mole) cc. hydrochloric acid were added drop-wise with stirring under nitrogen at 0–(–2)° C. The mixture was stirred for 22 hours at this temperature. Then the reaction mixture was allowed to warm up to 20–25° C. and 50 ml methylene chloride were added to the mixture. It was stirred for 10 minutes then the layers were separated. The organic layer was washed with 4×20 ml water and evaporated at 30° C.

The 17 g oily residue were dissolved in 50 ml acetone, then 17.4 g (0.1 mole) N-methyl-1-naphthalenemethylamine, 26 ml water, 12.9 g (17.5 ml, 0.1 mole) N,N-diisopropylethylamine and 2.22 g tetrabutylammonium-iodide were added. The mixture was stirred at room temperature for 1 hour under nitrogen and further for 6 hours under reflux. The obtained solution was cooled to 20–25° C. and the layers were separated. 40 ml acetone were added to the upper layer and then 10 ml cc. hydrochloric acid were added drop-wise at 16–20° C. The mixture was stirred at this temperature for 1 hour and further for 1 hour at 5–10° C. The product was filtered off, washed with 2×15 ml 5° C. water and 2×15 ml 5° C. acetone. The obtained product was air-dried at 40° C.

Yield: 13.1 g (40%).

Melting point 204–205° C.

Impurity (cis-isomer): 0.12%.

EXAMPLE 6

14.3 g 6,6-dimethyl-1-heptene-4-yn-3-ol were placed in a 250 ml flask, and 54 g (46 ml, 0.54 mole) cc. hydrochloric acid were added drop-wise with stirring under nitrogen at 0–(–2)° C. The mixture was stirred for 22 hours at this temperature. The temperature was allowed to warm up to 20–25° C. and 50 ml methylene chloride were added to the mixture. It was stirred for 10 minutes and the layers were separated. The organic layer was washed with 4×20 ml water and evaporated at 30° C.

The oily residue was dissolved in 50 ml methyl ethyl ketone, 17.4 g (0.1 mole) N-methyl-1-naphthalenemethylamine, 2.22 g tetrabutylammonium-iodide and 26 ml water were added, and the suspension was stirred for 1 hour at room temperature. It was stirred further for 2 hours with reflux, cooled to 20–25° C., and 40 ml methyl ethyl ketone were added. The organic layer was separated. At the same temperature, 10 ml cc. hydrochloric acid were added and the mixture was stirred for 1 hour. The obtained suspension was stirred for 4 hours at 0–4° C., then the product was filtered off and washed with 5 ml 5° C. methyl ethyl ketone. The obtained product was air-dried at 40° C.

Yield 11.7 g (38%).

Melting point 204–204° C.

Impurity (cis-isomer): 0.17%.

The invention relates to a new process for preparing the (E)-N-methyl-N-(1-naphthylmethyl)-6,6-dimethylhept-2-ene-4-ynyl-1-amine of formula (I) and the acid addition salts thereof.

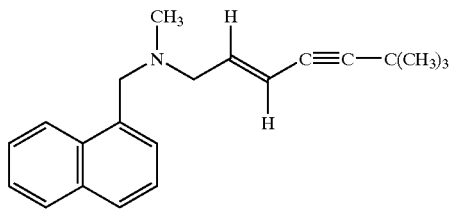

(I)

The compound of formula (I)—international nonproprietary (INN) name: terbinafine—was first disclosed in the European Patent Specification No. 24587 (priority: 22.08.1979) as a good antifungal agent used preferably against mycosis caused by dermathophytons on the skin and on the nail. Example 16 of this patent specification describes the specific compound and mentions that it is a trans isomer. According to the patent specification the terbinafine was prepared in three different chemical ways. It can be seen from the specification that the compound was always obtained in base form—namely as the mixture of cis(Z) and trans(E) isomers. The separation was achieved by column chromatography which is a procedure preferably not emoloved in a industrial large scale production.

In a later publication (see J. Med. Chem. 27, 1539–1543 (1984)) the hydrochloride salt of the trans isomer was obtained from the mixture of the base by way of column chromatography on silica-gel, and salt formation with hydrochloric acid in ethanol followed by recrystallization. After the success of terbinafine on the market more processes were published. Thus the process described in Swiss Patent Specification No. 678 537 or in its Hungarian equivalent Pat. No. 209 284 used as starting material the hydrochloride salt of N-methyl-1-naphthalenemethylamine of formula (II) and the geometric isomeric (E:Z) mixture of 3:1 of 1-bromo-6,6-dimethyl-hept-2-ene-4-yne of formula (IIIa)

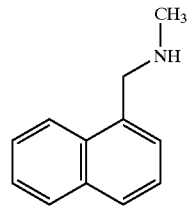

(II)

-continued

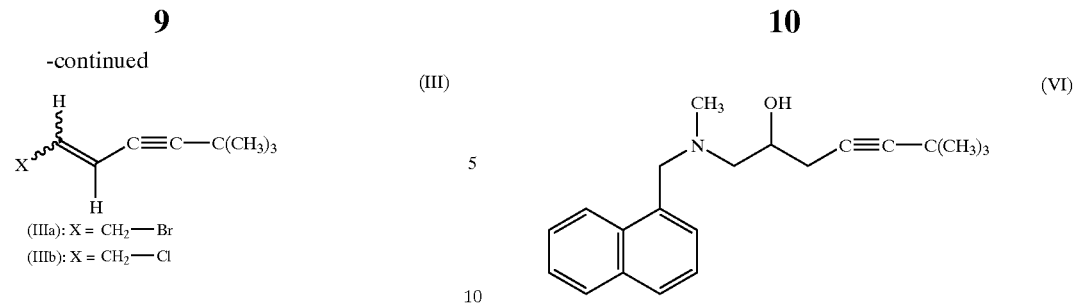

(IIIa): X = CH₂—Br
(IIIb): X = CH₂—Cl

The essence of the procedure is that the secondary amine was alkylated with the bromo-compound of formula (IIIa),—a crude product and mixture of geometric isomers—in the presence of aqueous sodium-hydroxide. The terbinafine base was formed as the mixture of trans- and cis-isomers in form of an oily substance. The crude terbinafine (still a mixture of isomers) was obtained by extraction with toluene and by evaporation of toluene, and had the same ratio of isomers as the compound of formula (IIIa). The crude terbinafine was then dissolved in ethyl acetate and hydrochloric acid gas was introduced into the solution. After stirring for a long time (4–15 hours) the precipitated hydrochloride salt of trans-terbinafine product of formula (I) was centrifuged, washed with ethyl acetate and dried.

The disadvantages of the process are the necessity to work with the offensive and unstable bromo-compound of formula (IIIa) and with the poisonous, aromatic solvent (extraction and evaporation of toluene), and that the preparation of the hydrochloride salt of terbinafine product requires dry hydrochloric acid gas and anhydrous ethyl acetate as solvent.

The compound of formula (IIIb) is an analogue of the known bromo-compound of formula (IIIa) (see European Patent Specification No. 341 048). It was prepared from known 3-hydroxy-6,6-dimethyl-hept-1-ene-4-yne of formula (IV), but no characteristic data of the chloro-compound of formula (IIIb) were described. (IIIb) was reacted directly, in from of a residue obtained by evaporation, with N-hydroxy-phthalimide. It is important to note that the chloro-compound of formula (IIIb) was not described elsewhere in the literature.

(IV)

(V)

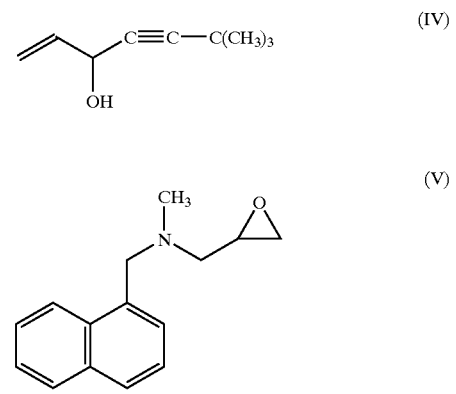

A different synthetic principle was applied in the preparation of terbinafine described in the Canadian Patent Specification No. 2 185 599. Here the epoxide of formula (V) was obtained from the secondary amine of formula (II) with an excess of epichlorohydrin, and (VI was converted into the secondary alcohol of formula (VI). Dehydration of the secondary alcohol of formula (VI) yielded a mostly undefined geometric isomeric mixture of (I).

(VI)

According to another process, the aldehyde derivative of formula (VII), obtained from the secondary amine of formula (II), was reacted with the phosphorus-compounds of formula (VIII) in a Wittig-type reactions. This process also resulted in an undefined isomeric mixture of the compound (I).

(VII)

(VIII)

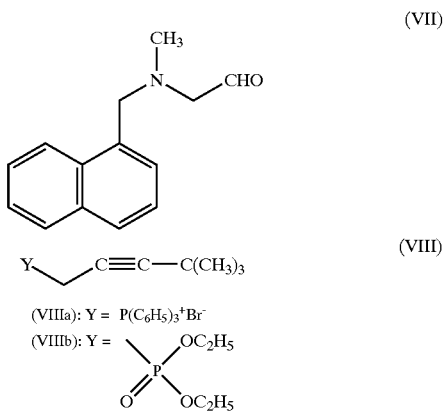

(VIIIa): Y = P(C₆H₅)₃⁺Br⁻
(VIIIb): Y =

The two processes above have several disadvantages:
  a large excess of reagents (epichlorohydrin, 3,3-dimethylbutyne) were required;
  occasionally, undefined amounts and ratios of reagents were used;
  complicated isolations by column chromatography were necessary;
  the product was obtained in form of a very disadvantageous (and eventually undefined) geometric isomeric mixture (E:Z 1:9→1:1).

The object of this invention is a process which does not have the disadvantages of the known processes and which is applicable for large scale production.

During our experiments it was surprisingly found that the acid addition salt of terbinafine may be prepared, without isolating the base form of compound of formula (I), by reacting the known secondary amine of formula (II) and the secondary alcohol of formula (IV) in a specific solvent.

This observation led to further unexpected results:
a) Reaction of the secondary alcohol of formula (IV) and cc. hydrochloric acid yields the chloro-derivative of formula (IIIb) quantitatively, whereas, in accordance with the procedure disclosed in the European Patent Specification No. 341 048 which employs thionyl chloride, this compound could only be obtained in a crude yield of 88%.
b) The quantitative formation of the compound of formula (IIIb) is surprising because the aqueous hydrogen chloride which is used for the preparation of (IIIb) is less reactive than the hydrobromic acid which is used for the preparation of the compound of formula (IIIa).

c) In the reaction with HCl instead of HBr, the less space requiring Cl-atom attaches to the end of the molecule. The trans:cis isomeric ratio obtained is not getting worse at all, it is even a little better (3:1→3.4:1).

d) It is also surprising that the reactivity of the chloro-compound of formula (IIIb) is similar, or even a little better than, the reactivity of the know bromo-analogue. Namely, the alkylation of the amine of formula (II) generated the product of formula (I) in a good yield.

e) The use of aliphatic ketones as a type of solvent gave an unexpected and surprising result. This solvent type is excellent for the extraction of the alkylating agent of formula (IIIb) and proved to be an effective solvent for the preparation of the compound of formula (I). Furthermore, when an aliphatic ketone, especially methyl isobutyl ketone, is used as A solvent, the hydrochloride salt of the end-product surprisingly precipitates after acidification with hydrogen chloride while the undesired hydrochloride salt of the cis-isomer and the other chemical impurities of the end-product remain in the solution and can be removed easily.

Table 1 summarizes the cis-isomer content of end-products obtained in different solvents. The results demonstrate that our surprising recognition, namely the advantageous use of an aliphatic ketone, especially methyl isobutyl ketone, afforded an especially low percentage of cis-isomer impurity.

Terbinafine base as a mixture of isomers of 75 w % trans and 25 w % cis was used as starting material.

TABLE 1

| Used solvent | Cis-isomer % of the obtained terbinafine salt |
| --- | --- |
| toluene | 10.7 |
| n-hexane | 11.7 |
| di-isopropyl-ether | 18.9 |
| ethanol | 10.6 |
| methyl isobutyl ketone | 0.19 |

Therefore, on the basis of the above goals, the invention is a new process for the preparation of the amine of formula (I) and acid addition salts thereof. This may be carried out as follows: the chloro-compound of formula (IIIb)—containing the E and Z isomers in a weight-ratio of 3.3–3.4:1—is prepared by reacting the secondary alcohol of formula (IV) with hydrogen chloride in a solvent. Then (IIIb) is reacted with the secondary amine of formula (II) in an aliphatic ketone-type solvent in the presence of a base and optionally a iodide salt catalyst. The (compound of formula (I) is obtained in base form and in an isomeric ratio of 3.3–3.4:1. The bate is converted directly into the hydrochloride salt by adding aqueous hydrogen chloride. The E-isomer-hydrochloride precipitates and is separated. Optionally the base can be liberated and can be converted—in a known way—into an acid addition salt with another pharmaceutically acceptable acid.

In a preferable embodiment of the process according to the invention 3–7 mole of the secondary alcohol of formula (IV) are reacted with preferably 5.0–5.5 mole, (preferably ice cooled, cc. hydrochloric acid. Conveniently, the reaction mixture is stirred overnight.

The chloro-compound of formula (IIIb) is obtained as a geometric isomeric mixture—the weight-ratio of trans:cis (E:Z) is 3.3–3.4:1-, and is extracted with an aliphatic ketone-type solvent, preferably methyl isobutyl ketone. Then the chloro-compound of formula (IIIb) extract is diluted with methyl isobutyl ketone and is reacted with the amine of formula (II). This alkylation reaction is carried out in the presence of an amine-base at 20–80° C. for 1–16 hours, preferably in the presence of equimolar N,N-diisopropylethylamine and 5–7 mole % iodide-salt catalyst for 3–5 hours.

The base form of the compound of formula (I) is obtained in solution in the phase of methyl isobutyl ketone, and is converted into a hydrogen-chloride salt by adding aqueous hydrochloric acid. The pH of the mixed two-phase system is adjusted to 1.0–3.0, preferably to 1.5–2.0. Then the two-phase system is cooled with stirring. The precipitated solid is filtered off, washed with water and with methyl isobutyl ketone and dried.

The obtained hydrochloride salt—containing the desired E isomer—treated with a bases e.g. ammonium-hydroxide, under mild conditions. The base of formula (I) obtained this way is converted into an acid addition salt by treatment with a pharmaceutically acceptable acid.

One of the starting materials of the process according to our invention, the secondary alcohol of formula (IV), is a known compound. This compound may be prepared e.g. according to the EP 24 587 Patent Specification using 3,3-dimethyl-1-butyne and acrolein. (See J. Med. Chem. 27, 1539–42 (1984))

The other starting material of the process according to our invention—the secondary amine of formula (II)—was described as a hydrochloride salt in Beilstein 12, II. 740, III. 3097, and IV. 2192.

Summarized, the process according to our invention has the following advantages:

1) The secondary alcohol of formula (IV) is converted into the alkylating chloro-compound of formula (IIIb) in a simple way by using cc. aqueous hydrogen chloride.

2) The compound of formula (IIIb) is obtained quantitatively from the reaction mixture by a single extraction with aliphatic ketone and can be reacted further in the same medium. The hydrochloride of the end-product of formula (I) simply precipitates from the aqueous-ketone, two-phase reaction mixture in the final acidification with hydrochloric acid.

3) The ketone, preferably methyl isobutyl ketone, used by us in the reaction steps has three functions in the process: it is an extracting agent, a solvent and finally a cosolvent, keeping the apolar, hardly water soluble impurities of the end-product in solution.

4) Compared to the processes of the prior art, our process is simple and suitable for large scale operations. The secondary alcohol of formula (IV) may be added to the apparatus and the hydrochloride of the compound of formula (I)—as the pure (E) trans isomer—is obtained at the end of the process.

5) While the processes of the prior art use hydrochloric acid gas for converting compound of formula (I), our process uses the more suitable aqueous hydrochloric acid.

6) In our process the hydrochloride salt of the end-product precipitates from a heterogeneous, two-phase (upper ketone, lower acid-aqueous) system. This provides for the high purity of the product obtained by the process according to the invention. The total impurity of the product (see Example 1, where it is 0.19%) la less, than the level of impurity obtained in the processes of the prior art (0.3%). Moreover the end-product does not contain—because it can not—bromide impurity.

7) Our process does not require expensive, anhydrous solvents.

EXAMPLE 1

Step A
Preparation of 1-chloro-6,6-dimethyl-hept-2-ene-4-yne 54 g (0.54 mole, 46 ml) cc. hydrochloric acid were added drop-wise to 13.82 g (0.1 mole) 6,6-dimethyl-hept-1-ene-4-yn-3-ol of formula (IV) with stirring and ice cooling at 2–6° C. After 8 hours stirring under ice-cooling the reaction mixture was further stirred overnight (15–16 hours).

40 g (50 ml) methyl isobutyl ketone were added to the two phase system. After separating the lower acid-water phase, the upper organic phase was extracted three times with 10 g water. After separating the aqueous phase the 1-chloro-6,6-dimethyl-hept-2-ene-4-yne of formula (IIIb) was obtained practically quantitatively—in the form of a mixture of trans-cis isomers—as an acid free methyl isobutyl ketone extract.

Step B
(E)-N-methyl-N-(1-naphthylmethyl)-6,6-dimethylhept-2-ene-4-ynyl-1-amine-hydrochloride 17.4 g (0.1 mole) N-methyl-1-naphthalenemethylamine of formula (II), 13.0 g (0.1 mole) N,N-diisopropylethylamine, 26 g ion free water and 22.22 g (0.006 mole) tetrabutylammonium-iodide were added in the given order to the methyl isobutyl ketone extract obtained in step A, and the mixtures was stirred from 4 hours at 70–80° C. The mixture was cooled to room temperature. After diluting with methyl isobutyl ketone the lower aqueous phase was separated. 15.5 g (13 ml) cc. hydrochloric acid were added drop-wise to the upper organic phase with stirring at 16–20° C.

After crystallization started, the reaction mixture was stirred for 1–2 hours at room temperature, then further for 1–2 hours at 2–6° C. The product was filtered off, washed twice with water, and once with methyl isobutyl ketone. After drying, 17.5 g (53.37%) terbinafine-hydrochloride salt were obtained (based on the secondary alcohol of formula (IV) used in Step A).

Melting point: 205–207° C.

Total impurity (by HPLC method): 0.19%.

EXAMPLE 2

The reaction was conducted in the same manner as Example 1 with the difference that the reaction described in Step B was carried out without tetrabutylammonium iodide.

Yield: 16.1 g (49.1%).

Melting pint: 205–207° C.

Total impurity (by HPLC method): 0.195%.

EXAMPLE 3

The reaction was conducted in the same manner as Example 1 with the difference that 17.5 g terbinafine-hydrochloride obtained in Step B were converted into the base by adding aqueous ammonia. The obtained product was reacted with 5 g lactic acid. 18.5 g terbinafine-lactate were obtained.

EXAMPLE 4

14.3 g 6,6-dimethyl-1-heptene-4-yn-3-ol (96%, equivalent to 0.1 mole 100%) were placed in a 250 ml flask. Then 54 g (46 ml, 0.54 mole) cc. hydrochloric acid were added drop-wise with stirring under nitrogen atmosphere at 0–(−2)° C. The reaction mixture was stirred for 22 hours at this temperature. Then the reaction mixture was allowed to warm to 20–25° C. and 40 ml methyl isobutyl ketone were added and stirred for 15 minutes at this temperature. The organic layer was separated, then washed with 4×20 ml water. Then 20 ml methyl isobutyl ketone, 17.4 g (0.1 mole) N-methyl-1-naphthylmethyl-amine, 12.9 g (17.5 ml, 0.1 mole) N,N-diisopropylethylamine, 26 ml water and 2.2 g tetrabutylammonium iodide were added under nitrogen during a period of 1 hour and stirred without cooling and heating. The mixture was heated to 70–80° C. and stirred for 1 hour. The reaction mixture was cooled to 20–25° C. and 40 ml methyl isobutyl ketone were added. The organic layer was separated and 10 ml hydrochloric acid. The mixture was stirred for 2 hours at this temperature after crystallization started. Then it was cooled to 5–10° C. and stirred for 1 hour.

The obtained crystals were filtered off, washed with 2×20 ml 5° C. water, then 2×20 ml 5° C. methyl isobutyl ketone. The wet product was suspended in the mixture of 100 ml methyl isobutyl ketone and 7 ml of water. 6.9 ml 25% ammonium-hydroxide were added drop-wise at 20–25° C. and stirred for 15 minutes. The solution was filtered though glass filter and the layers were separated. 9.2 ml 6 N hydrochloric acid was added drop-wise to the solution and stirred for 1 hour at this temperature, then further for 1 hour at 5–10° C. The product was filtered off, washed with 2×20 ml 5° C. water and 2×20 ml 5° C. methyl isobutyl ketone. The product was air-dried at 40° C.

Yield: 16.9 g (51.5%).

Melting point 204–205° C.

Impurity (cis-isomer): less than 0.1%.

EXAMPLE 5

14.3 g 6,6-dimethyl-1-heptene-4-yn-3-ol were placed in a 250 ml flask, and then 54 g (46 ml, 0.54 mole) cc. hydrochloric acid were added drop-wise with stirring under nitrogen at 0–(−2)° C. The mixture was stirred for 22 hours at this temperature. Then the reaction mixture was allowed to warm up to 20–25° C. and 50 ml methylene chloride were added to the mixture. It was stirred for 10 minutes then the layers were separated. The organic layer was washed with 4×20 ml water and evaporated at 30° C.

The 17 g oily residue were dissolved in 50 ml acetone, then 17.4 g (0.1 mole) N-methyl-1-naphthalenemethylamine, 26 ml water, 12.9 g (17.5 ml, 0.1 mole) N,N-diisopropylethylamine and 2.22 g tetrabutylammonium-iodide were added. The mixture was stirred at room temperature for 1 hour under nitrogen and further for 6 hours under reflux. The obtained solution was cooled to 20–25° C. and the layers were separated. 40 ml acetone were added to the upper layer and then 10 ml cc. hydrochloric acid were added drop-wise at 16–20° C. The mixture was stirred at this temperature for 1 hour and further for 1 hour at 5–10° C. The product was filtered off, washed with 2×15 ml 5° C. water and 2×15 ml 5° C. acetone. The obtained product was air-dried at 40° C.

Yield: 13.1 g (40%).

Melting point 204–205° C.

Impurity (cis-isomer): 0.12%.

EXAMPLE 6

14.3 g 6,6-dimethyl-1-heptene-4-yn-3-ol were placed in a 250 ml flask, and 54 g (46 ml, 0.54 mole) cc. hydrochloric acid were added drop-wise with stirring under nitrogen at 0–(−2)° C. The mixture was stirred for 22 hours at this temperature. The temperature was allowed to warm up to 20–25° C. and 50 ml methylene chloride were added to the mixture. It was stirred for 10 minutes and the layers were separated. The organic layer was washed with 4×20 ml water and evaporated at 30° C.

The oily residue was dissolved in 50 ml methyl ethyl ketone, 17.4 g (0.1 mole) N-methyl-1-naphthalenemethylamine, 2.22 g tetrabutylammonium-iodide and 26 ml water were added, and the suspension was stirred for 1 hour at room temperature. It was stirred further for 2 hours with reflux, cooled to 20–25° C. and 40 ml methyl ethyl ketone were added. The organic layer was separated. At the same temperature, 10 ml cc. hydrochloric acid were added and the mixture was stirred for 1 hour. The obtained suspension was stirred for 4 hours at 0–4° C., then the product was filtered off and washed with 5 ml 5° C. methyl ethyl ketone. The obtained product was air-dried at 40° C.

Yield 11.7 g (38%).

Melting point 204–204° C.

Impurity (cis-isomer): 0.17%.

What is claimed is:

1. A process for the preparation of (E)-N-methyl-N-(1-naphthylmethyl)-6,6-dimethylhept-2-ene-4-ynyl-1-amine of formula (I)

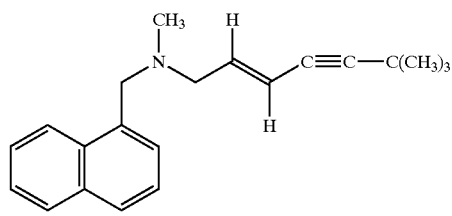

or an acid addition salt thereof, which comprises reacting a secondary alcohol of formula (IV)

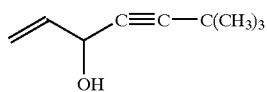

with hydrochloric acid to obtain a compound of formula (IIIb)

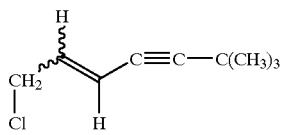

having an E:Z isomer ratio of 3.3–3.4:1,
reacting the compound of formula (IIIb) with a secondary amine of formula (II)

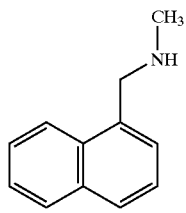

in an aliphatic ketone-type solvent in the presence of a base and optionally an iodide salt catalyst to obtain a reaction mixture comprising E and Z isomers of the compound of formula (I) in base form and in a ratio of E and Z isomers of 3.3–3.4:1, adding aqueous hydrochloric acid directly to the reaction mixture to obtain a precipitate of the hydrochloride salt of the compound of formula (I), separating the precipitated hydrochloride salt, and optionally liberating the compound of formula (I) in base form and converting said liberated base into a pharmaceutically acceptable acid addition salt.

2. A process according to claim 1, wherein the secondary alcohol of formula (IV) is reacted with 3–7 mole cc. aqueous hydrochloric acid to obtain the compound of formula (IIIb).

3. A process according to claim 1, wherein the compound of formula (IIIb) is reacted with the secondary amine of formula (II) in the presence of a base at from 20 to 80° C. for 1 to 16 hours.

4. A process according to claim 1, wherein the aliphatic ketone-type solvent is methyl isobutyl ketone.

5. A process according to claim 4, wherein the iodide salt catalyst is employed in an amount of 1–10 mole %.

6. A process according to claim 4, wherein 5–37% hydrochloric acid is added to the reaction mixture at 10–30° C., and the pH is adjusted to 1–3.

7. A process according to claim 1, wherein the secondary alcohol of formula (IV) is reacted with 5–5.5 mole cc. aqueous hydrochloric acid to obtain the compound of formula (IIIb).

8. A process according to claim 1, wherein the compound of formula (IIIb) is reacted with the secondary amine of formula (II) in the presence of N,N-diisopropylethylamine at from 70–8° C. for 3–5 hours.

9. A process according to claim 4, wherein the iodide salt catalyst is employed in an amount of 5–7 mole %.

10. A process according to claim 4, wherein 20–37% hydrochloric acid is added to the reaction mixture at 10–30° C., and the pH is adjusted to 1.5–2.

* * * * *

UNITED STATES PATENT AND TRADEMARK OFFICE
CERTIFICATE OF CORRECTION

PATENT NO. : 6,770,786 B1
DATED : August 3, 2004
INVENTOR(S) : Bod et al.

It is certified that error appears in the above-identified patent and that said Letters Patent is hereby corrected as shown below:

Column 16,
Line 47, "from 70-8° C" should read -- from 70-80° C --.

Signed and Sealed this

Twenty-ninth Day of March, 2005

JON W. DUDAS
*Director of the United States Patent and Trademark Office*